(12) United States Patent
Gross

(10) Patent No.: US 7,178,746 B2
(45) Date of Patent: Feb. 20, 2007

(54) SHOWER COMPRISING A LIGHTING DEVICE

(75) Inventor: Juergen Gross, Steinach (DE)

(73) Assignee: Hansgrohe AG, Schiltach (DE)

( * ) Notice: Subject to any disclaimer, the term of this patent is extended or adjusted under 35 U.S.C. 154(b) by 0 days.

(21) Appl. No.: 10/549,013

(22) PCT Filed: Mar. 19, 2004

(86) PCT No.: PCT/EP2004/002869

§ 371 (c)(1),
(2), (4) Date: Sep. 12, 2005

(87) PCT Pub. No.: WO2004/082846

PCT Pub. Date: Sep. 30, 2004

(65) Prior Publication Data

US 2006/0175437 A1    Aug. 10, 2006

(30) Foreign Application Priority Data

Mar. 19, 2003   (DE) ................................ 103 12 866

(51) Int. Cl.
*B05B 1/14*   (2006.01)
(52) U.S. Cl. ................. 239/552; 239/18; 239/211; 239/282; 239/289; 239/530; 239/556; 362/96
(58) Field of Classification Search ............. 239/16–18, 239/211, 282, 283, 289, 530, 548, 552, 556–558; 362/96, 806
See application file for complete search history.

(56) References Cited

U.S. PATENT DOCUMENTS

| | | | | |
|---|---|---|---|---|
| 1,818,319 A | * | 8/1931 | Good ........................... | 239/18 |
| 4,564,889 A | * | 1/1986 | Bolson ......................... | 362/96 |
| 4,616,298 A | * | 10/1986 | Bolson ......................... | 362/96 |
| 5,165,777 A | * | 11/1992 | Kira ............................. | 362/96 |
| 5,207,499 A | * | 5/1993 | Vajda et al. .................. | 362/96 |
| 6,021,960 A | | 2/2000 | Kehat | |
| 6,126,290 A | | 10/2000 | Veigel | |
| 6,439,472 B1 | | 8/2002 | Lin et al. | |
| 6,607,144 B1 | * | 8/2003 | Yen .............................. | 239/18 |
| 6,637,676 B2 | | 10/2003 | Zieger et al. | |
| 6,644,561 B1 | * | 11/2003 | Daane .......................... | 239/18 |
| 2002/0158153 A1 | * | 10/2002 | Zieger et al. ............... | 239/548 |

FOREIGN PATENT DOCUMENTS

| | | |
|---|---|---|
| DE | 201 01 460 U1 | 1/2001 |
| DE | 201 01 460 U | 7/2001 |
| DE | 201 21 306 U | 6/2002 |
| EP | 1 239 089 A2 | 11/2002 |
| WO | WO 91/12896 A | 9/1991 |

OTHER PUBLICATIONS

German Search Report, May 11, 2004.

* cited by examiner

*Primary Examiner*—Steven J. Ganey
(74) *Attorney, Agent, or Firm*—Duane Morris LLP

(57) ABSTRACT

The invention relates to a shower comprising a jet-discharge disk (4). Behind said jet-discharge disk a flat water-filled chamber (7) is occluded on the side facing away from the jet-disk by a transparent to translucent bottom (2). The shower is provided with a lighting device (13) which is arranged in such a manner as to emit light through the bottom (2), the chamber (7) and the jet-disk (4).

16 Claims, 1 Drawing Sheet

SHOWER COMPRISING A LIGHTING DEVICE

Figure 1:
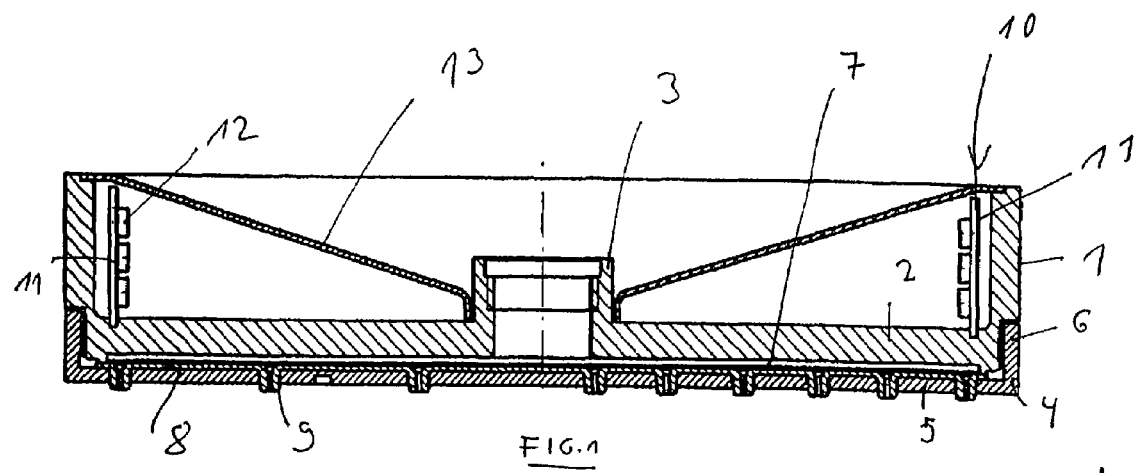

The invention is based on a shower head having a housing, a water-inlet fitting, and a jet-discharge disk, from which water exits in the form of several, or numerous, jets.

It has long been known that the types of jets coming from shower heads may be varied in order to enhance feelings of well-being during showering, and for medical reasons. Massage jets, weak, aerated jets, and powerful jets, any of which may also be provided in combination, or sequentially by automatic selectors that switch between the various types of jets, are available.

Varying water temperature is another means for improving health and enhancing feelings of well-being.

That light may affect people's feelings of well-being has also been recognized.

Generating variable lighting effects within shower stalls is thus known. Shower heads that have lighting devices are also known. Shower heads having lighting devices are also known. However, either their lighting effects are weak, or they are very large, in particular, have very large heights.

The problem addressed by the invention is creating shower heads that will allow generating such variable lighting effects during showering, and both provide visually impressive displays and be utilizable in a wide variety of manners.

In order to solve that problem, the invention proposes a shower head having those features stated under claim 1. Elaborations on the invention are covered by subclaims.

The lighting device generates an illumination that thus emanates from the shower head itself and propagates in the same directions as the jets of water exiting the shower head, which, to the user, is indistinguishable from a normal shower head, that is, a shower head lacking a lighting device, when not in use. According to the invention, under an elaboration thereon, it may be provided that the lighting device will be switched on only while the shower head is in use. Since light exits from the jet-discharge disk, water exiting the exit apertures, which, of course, will still exit it in the form of isolated jets, will effectively be illuminated from within, yielding a visually impressive display.

An interesting display is created when light, for example, exits exclusively, or predominantly, from the apertures in the jet-discharge disk, where the jet-discharge disk may be configured such that it is opaque, which will cause light to exit exclusively from those apertures from which jets of water also exit.

However, it will also be feasible to have, and the invention proposes that, light exit from large sections of the jet-discharge disk that, for example, are noncontiguous, where "large" means larger than the areas of the apertures from which jets of water exit.

In further elaborating on the invention, it may be provided that light essentially exits from the entire area of the jet-discharge disk, in which case, it may also be provided that light exiting the apertures from which jets of water exit will be more intense than light transmitted at other locations thereon, which, for example, may be accomplished by configuring the jet-discharge disk such that it is translucent, and thus will attenuate transmitted light somewhat.

According to the invention, an additional lamp may also be arranged within the shower head, where that lamp is preferably either situated on its centerline, centered on its exit surface, or is annular in shape and extends around its circumference.

In further enhancing the visual display that occurs when the shower head is used, it may be provided that a chamber, into which the water-inlet leads, is configured upstream of the jet-discharge disk. That chamber may be totally filled with water while the shower head is in use. According to the invention, the lighting device may then be arranged upstream of that chamber in order that light emanating from the lighting device will transit the chamber and exit through the jet-discharge disk.

A transparent to translucent wall that will allow generating various types of lighting effects, depending upon how transparent it is and any patterning that may be present thereon, may preferably be arranged between the chamber filled with water and the lighting device.

The chamber's thickness, that is, its dimension orthogonal to the surface of the jet-discharge disk, may also be utilized for influencing lighting effects. The invention proposes that the chamber have a uniform thickness over its full lateral extension in order to allow arriving at lighting effects whose intensities will be as uniform as possible over the full lateral extension of the jet-discharge disk.

In elaborating on the invention, the lateral dimension(s) of the chamber is/are identical to that/those of the jet-discharge disk. In other words, the entire chamber is arranged upstream of the jet-discharge disk and preferably has the same thickness over its full lateral extension.

In elaborating on the invention, it may be provided that the lateral dimensions of the jet-discharge disk along either of a pair of mutually orthogonal axes are identical, i.e., that the jet-discharge disk is, for example, circular or square.

The invention proposes that the chamber filled with water arranged upstream of the jet-discharge disk be configured such that it is very thin, for example, have a thickness equaling 1%–10% of the diameter, or other lateral dimension, of the jet-discharge disk. Due to that rather thin configuration of the chamber, streamlines, turbulences, or similar that will yield very impressive lighting effects will occur upstream of the jet-discharge disk.

Those displays will be further enhanced if, in elaborating on the invention, the chamber and/or the jet-discharge disk are arranged such that hydrodynamic turbulences and/or flow fields with radial streamlines will be promoted within the chamber.

Moreover, since the volume of the chamber is very small, it is highly unlikely that, due to capillarity, it will remain filled with water after the water supply to the shower head is shut off, which will reduce hazards that bacterial growth will occur therein during extended periods of disuse.

According to the invention, it may be provided that the lighting device contains LEDs. The latter may be arranged in tight spaces and are capable of emitting colored light. According to another feature of the invention, the color of the emitted light may be employed as a design element. Suitably controlling the LEDs will allow generating arbitrary color variations.

It has been found that a radial arrangement of the LEDs yields a particularly uniform emission of colored light. Both for that reason, and in order to allow configuring the shower head such that it will have a low profile, according to the invention, it may be provided that the lighting device has radially emitting light sources, that is, light sources that emit light propagating parallel to the jet-discharge disk that may then be deflected to the jet-discharge disk by a deflection device, a mirror, or similar.

That radial arrangement, together with the deflection device, yield a thin structure, which is why the shower head may also be configured in the form of a side-mounting shower head for installation on, for example, the wall of a shower stall, or as a hand-held shower head, instead of merely in the form of-an overhead shower head, which would be the obvious choice.

Figure 2:
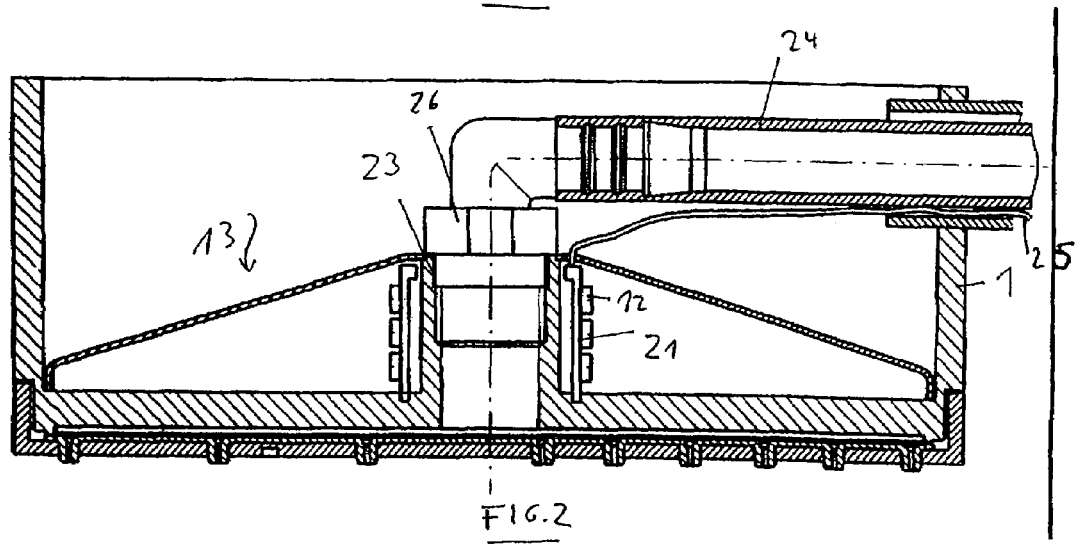
Figure 3:
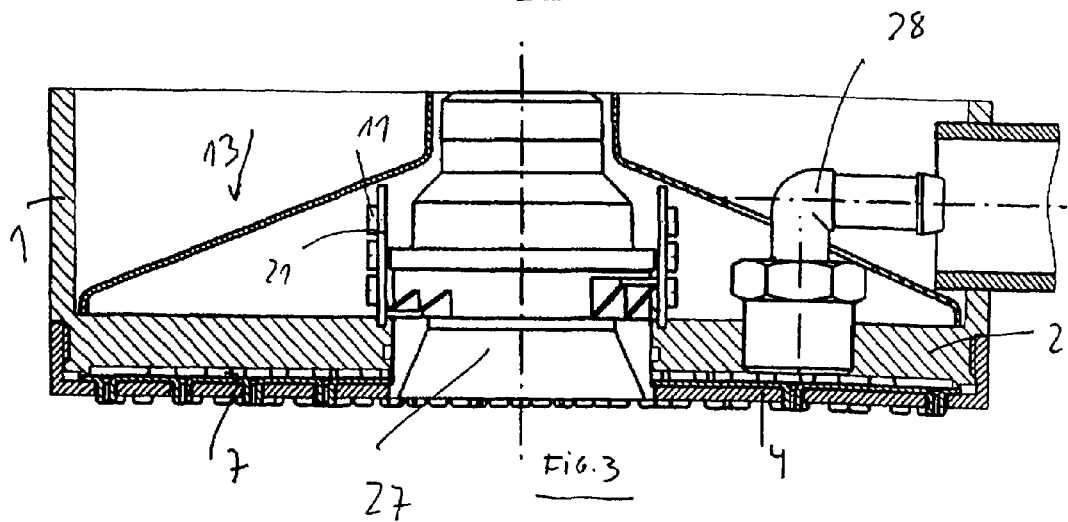

Other features, details, and benefits of the invention will be evident from the claims and the abstract, the wordings of both of which are herewith made an integral part of this description by way of reference thereto, the following descriptions of preferred embodiments thereof, and the figures, which depict:

FIG. 1 a sectioned view of a first sample embodiment of a shower head according to the invention;

FIG. 2 a sectioned view of a second sample embodiment of a shower head according to the invention;

FIG. 3 a sectioned view of a third sample embodiment of a shower head according to the invention.

FIG. 1 depicts a sectioned view of a schematized shower head. The shower head contains a housing 1 in the form of a short cylinder having a bottom 2. A fitting 3 is inserted into the center of its bottom from the latter's upstream side, that is, from above in FIG. 1. That fitting 3 is used for attaching a supply line.

A jet-discharge disk 4 that is also in the form of a plate 5 having a cylindrical rim 6 is arranged on the other side of the bottom 2 of the shower head's housing 1. That rim 6 is used to attach the jet-discharge disk 4 to the bottom end of the shower head's housing 1 such that a thin, vacant space forming a chamber 7 remains between the bottom 2 of the housing 1 and the jet-discharge disk. A gasket that, however, may also be formed by a plate 8 consisting of an elastic material, may be present between the cylindrical rim 6 and the base 2 of the shower head's housing 1. The plate 8 has nozzles 9 that protrude through associated apertures in the jet-discharge disk 4 formed onto it. The plate 8 is fabricated from a transparent or translucent material. The bottom 2 of the shower head's housing 1 is also fabricated from a transparent or translucent material.

The line fitting 3 leads directly into the chamber 7. Water entering the chamber 7 through the fitting 3 will distribute itself throughout the entire chamber 7 and then flow out of the nozzles 9. In the case of the problems addressed here, it is not necessary that the nozzles 9 be formed onto the plate 8 fabricated from an elastic material. A jet-discharge disk 4 that has simple through holes serving as rigid exit apertures might also be present.

A lighting device 10 consisting of either a number of discrete components or a continuous strip is arranged on a plate 11 extending around the inner wall of the shower head's housing 1, upstream of the bottom 2 thereof. The plate 11 contains three overlapping rows of LEDs 12 that may, for example, emit light of varying colors. The LEDs emit light radially inward from the plate 11, that is, toward the arrangement's symmetry axis.

A deflection device 13 that is formed from a flattened cone whose apex points toward the bottom end of the shower head's housing 1 is arranged upstream of the bottom 2 of the shower head's housing 1, where the deflection device 13 has a central aperture that serves to center the deflection device on the fitting 3 for admitting water and attach it thereto.

When the lighting device 10 is switched on, light emitted by the LEDs 12 will be deflected by the deflection device 13 such that the light beams emitted therefrom will be incident normally on the bottom 2 of the housing, pass through it, and then exit through the jet-discharge disk 4. Those light beams may either exit over the entire area of the jet-discharge disk, or exit only through the open apertures therein, depending upon the nature of the material from which the jet-discharge disk is fabricated. If they exit from those apertures, they will automatically propagate through the jets of water exiting therefrom, yielding an impressive display.

In the case of the embodiment depicted in FIG. 2, the fitting 23 for attaching the supply line 24 is somewhat larger and the supply line 24 has been shown. The latter enters through the rim of the shower head's housing 1 in the form of a length of pipe. A line 25 supplying electric power is fed through at the same location. In the case of this embodiment, the lighting device is arranged around the central line fitting 23, which contains a plate or a cylinder 21, on which the LEDs 12 are arranged. In this case, the latter emit radially outward. Once again, the deflection device 13 contains a flattened cone fabricated from a material whose inner surface is reflective. In this case, the flattened cone is oriented such that its apex points away from the jet-discharge disk. Once again, it is centered on the fitting, and is held in place by a nut 26.

FIG. 3 depicts an embodiment that has a large aperture in the center of the jet-discharge disk 4 that has a lamp 27 situated therein. The bottom end of the lamp is flush with the outer surface of the jet-discharge disk 4. Once again, a deflection device 13, similar to that of the embodiment depicted in FIG. 2, is present. The lighting device also corresponds to that of FIG. 2. In this case, the line supplying water exiting the shower head is arranged off-center and screwed into the transparent bottom 2 of the housing 1 from its upstream side using a pipe elbow 28 having an external thread on one end. Here, once again, a very thin chamber 7 that contains conducting devices, if necessary, in order to distribute water throughout the chamber such that it will exit from the nozzles in the form of uniform jets extending over the entire area of the jet-discharge disk, is formed.

What is claimed is:

1. A shower head, comprising:
   a housing,
   a water-inlet fitting for admitting water to the shower head,
   a jet-discharge disk having a number of apertures from which jets of the water exit from the shower head, and
   a lighting device arranged such that light exits from the shower head at the jet-discharge disk,
   wherein the water inlet fitting leads to a chamber in the shower head arranged upstream of the jet-discharge disk,
   the lighting device is arranged upstream of the chamber,
   the side of the chamber facing the lighting device is bounded by a wall that is one of transparent and translucent, and
   the lighting device has radially emitting light sources and a deflection device.

2. A shower head according to claim 1, wherein light from the lighting device exits at least predominantly from the jet-discharge disk.

3. A shower head according to claim 1, wherein the light from the lighting device exits from large, non-contiguous sections of the jet-discharge disk.

4. A shower head according to claim 1, wherein light from the lighting device essentially exits from an entire surface of the jet-discharge disk.

5. A shower head according to claim 1 having a lamp centrally arranged in the jet-discharge disk.

6. A shower head according to claim 1, wherein the chamber has a thickness that is approximately uniform over a full lateral extension of the chamber.

7. A shower head according to claim 1, wherein the chamber has at least one lateral dimension that is approximately equal to at least one lateral dimension of the jet-discharge disk.

8. A shower head according to claim 1, wherein the jet-discharge disk is one of circular and square.

9. A shower head according to claim 1, wherein the chamber has a thickness that is much less than any lateral dimension of the chamber.

10. A shower head according to claim 1, wherein at least one of the chamber and the jet-discharge disk is configured such that hydrodynamic turbulences occur in the chamber.

11. A shower head according to claim 1, wherein at least one of the chamber and the jet-discharge disk is configured such that a flow field with radial streamlines occurs within the chamber.

12. A shower head according to claim 1, wherein the lighting device comprises LEDs.

13. A shower head according to claim 1, wherein the lighting device comprises light sources emitting light of various colors.

14. A shower head according to claim 1, wherein the shower head is configured as an overhead shower head.

15. A shower head according to claim 1, wherein the shower head is configured as a side-mounting shower head.

16. A shower head according to claim 1, wherein the shower head is configured as a hand-held shower head.

* * * * *